(12) United States Patent
Mansmann (10) Patent No.: US 7,476,250 B1
(45) Date of Patent: Jan. 13, 2009

(54) SEMI-PERMEABLE MEMBRANES TO ASSIST IN CARTILAGE REPAIR

(76) Inventor: Kevin A. Mansmann, 250 W. Lancaster Ave., Suite 310, Paoli, PA (US) 19301

( * ) Notice: Subject to any disclaimer, the term of this patent is extended or adjusted under 35 U.S.C. 154(b) by 0 days.

(21) Appl. No.: 09/544,341

(22) Filed: Apr. 6, 2000

Related U.S. Application Data (60) Provisional application No. 60/127,905, filed on Apr. 6, 1999.

(51) Int. Cl.
*A61F 2/08* (2006.01)

(52) U.S. Cl. ............................. 623/14.12; 623/23.72

(58) Field of Classification Search ............ 424/93.7, 424/424; 435/297.1, 297.5, 1.1, 1.2; 623/13, 623/18.11; 606/151
See application file for complete search history.

(56) References Cited

U.S. PATENT DOCUMENTS

| | | | | |
|---|---|---|---|---|
| 4,161,948 A | * | 7/1979 | Bichon | 602/58 |
| 4,495,288 A | * | 1/1985 | Jarvis, Jr. et al. | 435/382 |
| 5,125,894 A | * | 6/1992 | Phipps et al. | 604/20 |
| 5,629,084 A | * | 5/1997 | Moya | 428/315.7 |
| 5,713,374 A | * | 2/1998 | Pachence et al. | 128/898 |
| 5,749,874 A | * | 5/1998 | Schwartz | 606/75 |
| 5,820,882 A | * | 10/1998 | Hubbell et al. | 424/491 |
| 5,834,005 A | * | 11/1998 | Usala | 424/424 |
| 6,080,194 A | * | 6/2000 | Pachence et al. | 623/23.76 |
| 6,264,695 B1 | * | 7/2001 | Stoy | 623/17.16 |
| 6,319,712 B1 | * | 11/2001 | Meenen et al. | 435/395 |
| 6,379,367 B1 | * | 4/2002 | Vibe-Hansen et al. | 606/151 |
| 6,387,693 B2 | * | 5/2002 | Rieser et al. | 435/297.1 |
| 6,458,159 B1 | * | 10/2002 | Thalgott | 623/17.11 |
| 6,528,052 B1 | * | 3/2003 | Smith et al. | 424/93.7 |
| 6,530,956 B1 | * | 3/2003 | Mansmann | 623/18.11 |

* cited by examiner

*Primary Examiner*—William H. Matthews
(74) *Attorney, Agent, or Firm*—Patrick D. Kelly

(57) ABSTRACT

A semi-permeable membrane can be used to promote the surgical repair of cartilage in a damaged or diseased joint, such as a knee, hip, or shoulder. In one method, the semi-permeable membrane is secured to the "articulating" surface (the exposed surface, as opposed to the "anchoring" surface which rests on a condyle) of a resorbable fibrous matrix that has been seeded, before implantation, with chondrocyte or similar cells that generate cartilage. A membrane used in this manner can help protect the cells as they grow, reproduce, and secrete new cartilage inside the resorbable matrix. In another method, the semi-permeable membrane is secured to a slightly damaged surface of a cartilage segment that is suffering from a condition known as chondromalacia, without using an underlying implanted matrix or other device. In a slightly different use, a semi-permeable membrane as disclosed herein can be used in conjunction with a cell-growing scaffold that is being used to generate tissue to repair or supplement an internal organ, such as a liver, spleen, pancreas, or possibly a heart.

2 Claims, 3 Drawing Sheets

LEGEND:
- ○ SAPL
- ○ Lubricen
- ∞ Lubricen/SAPL complexes
- ● Hyaluronic acid
- ⊕ Other macromolecules
- ⋮⋮⋮ Semi-permeable membranes

Fig. 6A
UNLOADED JOINT SPACE

Fig. 6B
INSTANTANEOUS LOADING

Fig. 6C
STATIC COMPRESSION

Fig. 6D
HYDROPLANING MOTION

Fig. 6E
LOADED FLUID FLOW THROUGH SELECTIVELY PERMEABLE MEMBRANES

SEMI-PERMEABLE MEMBRANES TO ASSIST IN CARTILAGE REPAIR

RELATED APPLICATIONS

This application claims priority based on provisional patent application 60/127,905, filed Apr. 6, 1999, and on utility application Ser. No. 09/393,522, filed Sep. 10, 1999 now U.S. Pat. No. 6,530,956.

BACKGROUND OF THE INVENTION

This invention is in the field of surgery, especially surgery to repair cartilage in joints such as knees, shoulders, or hips.

Background information on knee, hip, and shoulder joints, on cartilage tissue, and on "classical" techniques and devices that have been used for many years for surgical repair of damaged cartilage are discussed in numerous medical texts, such as *Campbell's Operative Orthopedics*, a five-volume treatise. Additional information is periodically issued by the American Academy of Orthopedic Surgeons in a series of books called "Orthopedic Knowledge Updates"; volume 6 in that series was issued in 1999.

As used herein, terms such as "surgery" and "surgical" include arthroscopic or other "minimally invasive" procedures which can be used to cut through tissue and insert a flexible membrane into a joint or other region of a limb or body.

The parent utility application cited above, Ser. No. 09/393,522, focuses mainly upon resorbable "scaffold" devices which can be used to help transplanted cells (mainly "chondrocyte" cells, which generate and secrete cartilage) generate new cartilage in a damaged joint such as a knee, hip, or shoulder. These improved scaffolds are inserted into a cartilage segment, such as on a femoral runner or tibial plateau inside a knee, in an area where a chunk of damaged cartilage has been removed. Briefly, the improved matrices use two different types of porous matrix materials. Both types of material are made of three-dimensional fibrous materials (such as collagen, the main type of fibrous protein which holds mammalian tissue together), but the two types of material have substantially different mechanical properties, mainly due to variations in fiber and crosslinking density, which can be manipulated and controlled during the manufacturing process. A relatively dense and stiff material, designed to withstand and resist a compressive load, is placed around the rim of the device and in internal "runners". A softer and more open and porous matrix material, designed to promote maximally rapid generation of new cartilage, is nestled within the protected zones that are created by the denser load-resisting rim and runners.

That is just a brief overview; the contents of that application Ser. No. 09/393,522, are hereby incorporated by reference, as though fully set forth herein.

Application Ser. No. 09/393,522 also describes an advanced type of semi-permeable outer membrane that can be attached to the "articulating" outer surface of an implanted resorbable scaffold as described above. The scaffold will support the outer membrane with a degree of stiffness and resiliency that allows the membrane to mimic a healthy cartilage surface, which is also semi-permeable.

That type of semi-permeable membrane can be used independently of implantable resorbable scaffolds. For example, if properly implanted and secured, it can be used as a covering and protective layer for mildly damaged native cartilage which is suffering from certain types of abrasion and similar damage referred to by physicians as "chondromalacia".

Accordingly, that type of surgically-implantable membrane is the subject of this current application, regardless of whether it is implanted along with and on top of a resorbable matrix, or attached as a protective surface layer to the top of mildly damaged cartilage.

One object of this invention is to disclose an improved semi-permeable membrane which can emulate and effectively replace the articulating surface of natural cartilage, for use in surgical repair of joints such as knees.

Another object of this invention is to disclose an improved type of semi-permeable membrane which can be used with any of a variety of resorbable matrix devices, including but not limited to the dual-material scaffolds described above, to increase the benefits offered by such devices for using transplanted cells to generate new cartilage inside a damaged joint.

Another object of this invention is to disclose an improved type of semi-permeable membrane which can be secured directly to an articulating cartilage surface that has been mildly damaged, such as by chondromalacia, to help protect and in some cases stimulate repair of such cartilage.

Another object of this invention is to disclose an improved type of semi-permeable membrane which can be used along with cell-growing scaffolds or other matrices that are being used to help replace or supplement tissue in an internal organ, such as a liver, spleen, pancreas, and possibly a heart.

These and other objects of the invention will become more apparent through the following summary, drawings, and description of the preferred embodiments.

SUMMARY OF THE INVENTION

A semi-permeable membrane can be used to promote the surgical repair of cartilage in a damaged or diseased joint, such as a knee, hip, or shoulder. In one method, the semi-permeable membrane is secured to the "articulating" surface (the exposed surface, as opposed to the "anchoring" surface which rests on a condyle) of a resorbable fibrous matrix that has been seeded, before implantation, with chondrocyte or similar cells that generate cartilage. A membrane used in this manner can help protect the cells as they grow, reproduce, and secrete new cartilage inside the resorbable matrix. In another method, the semi-permeable membrane is secured to a slightly damaged surface of a cartilage segment that is suffering from a condition known as chondromalacia, without using an underlying implanted matrix or other device. In a slightly different use, a semi-permeable membrane as disclosed herein can be used in conjunction with a cell-growing scaffold that is being used to generate tissue to repair or supplement an internal organ, such as a liver, spleen, pancreas, or possibly a heart.

DESCRIPTION OF THE PREFERRED EMBODIMENTS

There are three different approaches for using a semi-permeable membrane as disclosed herein. Briefly, one approach involves placement of a membrane on top of a porous resorbable scaffold implant that will support the creation of new cartilage by transplanted chondrocyte and similar cells that are "seeded" into the porous matrix material before or during the implant surgery. This cartilage regenerating approach can be used to repair a cartilage defect that extends into the underlying layers of the cartilage segment.

A second approach involves placing and securing a semi-permeable membrane directly on top of native cartilage that has suffered relatively mild abrasion or similar damage to a surface area only. This type of superficial damage is often referred to be physicians as chondromalacia. If it can be stopped, it will not lead to increasing levels of damage to the cartilage. However, if this type of surface abrasion is not properly treated, the abraded surface of one cartilage segment tends to begin acting as an roughened abrasive surface, and it typically begins to inflict abrasion damage on the surface of the cartilage segment which articulates against it (for example, a slightly abraded femoral runner which no longer has a completely smooth surface can begin to damage the tibial plateau that the femoral runner rubs against). By securing a membrane as disclosed herein on top of a mildly abraded cartilage surface, that type of damage process can be treated and either slowed or terminated.

A third potential approach for using a semi-permeable membrane as disclosed herein does not involve cartilage repair at all; instead, it involves the use of a semi-permeable membrane to cover and interact with a cell-growing scaffold or other type of matrix (made out of collagen or resorbable polymeric fibers) that is being used to help repair, replace, or supplement tissue in internal organs, such as a liver, spleen, pancreas, or possibly even heart tissue.

These three approaches are discussed under separate sub-headings, below.

Use of Membrane on Top of Scaffold Implant

Figure 1:
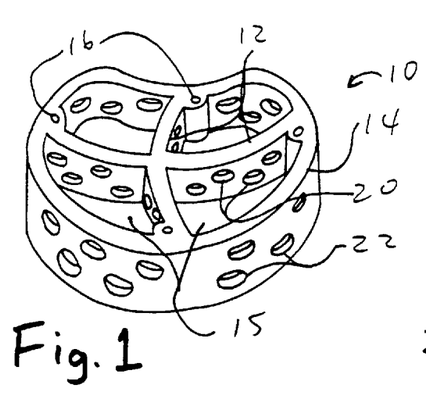
FIG. 1 depicts a scaffold 10 made of a relatively stiff matrix material, to help repair a damaged segment of cartilage on a tibial plateau. The internal runners and outer rim divide the scaffold into four cell-growth compartments, each of which covers an area less than 1 square centimeter.
Figure 2:
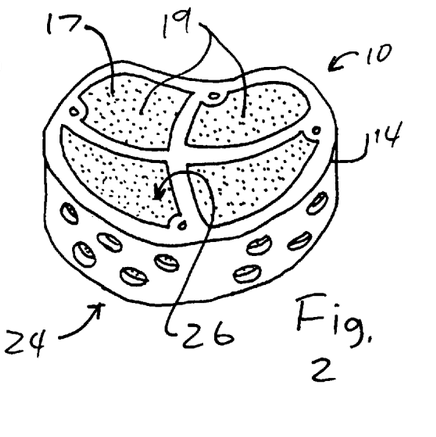
FIG. 2 depicts the same scaffold 10 shown in FIG. 1, with the four internal compartments filled with four segments of a matrix material which has greater porosity, for maximal rates of cell growth and cartilage secretion within those compartments.

Referring to the drawings, callout number 10 in FIGS. 1 and 2 refers to a implantable scaffold made of a porous material that supports cell growth. The underlying scaffold device will be described first, then the semi-permeable membrane which provides a surface covering on the "articulating" surface of the scaffold will be described.

Scaffold 10 comprises several relatively dense and stiff walls, shown in FIG. 1 as internal runners 12 and an outer rim 14. These walls are designed to resist and withstand a compressive load, such as when the patient begins to puts his or her weight on the knee, hip, or other joint.

The rim 14 and runners 12 interact to divide scaffold 10 into 4 internal compartments 15. These compartments 15 are filled with a more open and porous matrix material 19, shown in FIG. 2. Since the highly porous material 19 does not need to withstand the types of compressive loads that arise when weight is imposed on a knee, hip, or other joint, it can be designed and manufactured in a way that maximizes the rates of cell growth and cartilage secretion by chondrocyte or similar cells. Such cells are "seeded" into a matrix of this type, before the device is surgically implanted in a damaged or diseased joint, or possibly during surgery. To stimulate cell growth and cartilage secretion, certain specialized hormones, growth factors, and nutrients can also be used, as described in various patents such as U.S. Pat. No. 5,041,138 (Vacanti et al 1991) and U.S. Pat. No. 5,206,023 (Hunziker 1993).

FIGS. 1 and 2 also show "runner vents" 20, which pass through the walls of the internal runners 12. These vents can promote the generation of "bridges" of cartilage between the internal compartments 15; as the runners 12 are gradually dissolved and resorbed, the bridges can help increase stabilizing interconnections between the cartilage segments being generated in the internal compartments 15. "Rim vents" 22 also pass through the outer rim 14, to allow transplanted chondrocyte cells to generate bridges of cartilage between the internal compartments and the surrounding cartilage.

Scaffold 10 shown in FIG. 2 has an anchoring surface 24, and an opposed "articulating" surface 26. The anchoring surface 24 will be pressed against, and anchored to, a condyle (which may be either a hard bone surface, or a layer of cartilage on top of a hard bone surface). The articulating surface 26 will remain exposed after the scaffold 10 has been anchored to a bone. It is this articulating surface 26 that will be covered by a semi-permeable membrane. This membrane is not shown in FIGS. 1 and 2, since it would hide the components and structure of the underlying scaffold 10.

The phrase "articulating surface" refers to the well-known fact that, in a healthy joint, two cartilage-covered surfaces on two different bones will rub, slide, roll, or otherwise move while in contact with each other, as the joint is flexed or extended. This type of mobile interaction between two such surfaces is referred to as articulation, and the two cartilage-covered surfaces that contact and press against each other during such motion are said to "articulate".

Figure 3:
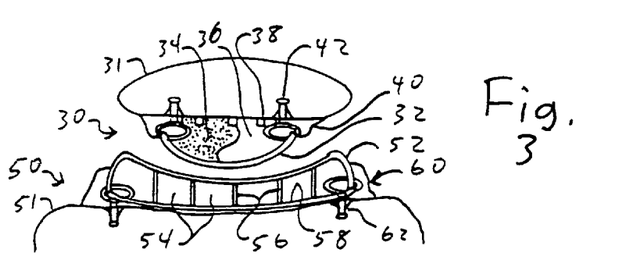
FIG. 3 is a cross-sectional view showing a femoral implant and a patellar implant, which interact with each other inside a knee. Each implant is covered by an exposed membrane, so that the two membranes press, slide, and "articulate" against each other when the joint is flexed or extended.

FIG. 3 illustrates this concept, by showing two scaffold-plus-membrane implants that will press and slide against each other in a femoral-patellar compartment (i.e., the interface between the thighbone and the kneecap). The lower part of FIG. 3 depicts a femoral scaffold assembly 50, with a row of compartments 54 that are separated from each other by a series of parallel runners 56. The runners 56 are bonded to and support an articulating membrane 52. Similarly, articulating membrane 32 covers patellar scaffold 30, and rests on top of a series of parallel load-sharing runners 36, one of which is shown in a partial cutaway view. The patellar runners 36 are oriented perpendicular to the femoral runners 56, in order to minimize the risk of any catching, grabbing, or other undesired interactions between the two sets of runners (patellar and femoral) as they press and slide against each other during articulation.

When the knee joint is being moved, the patellar membrane 32 and the femoral membrane 52 will move, slide, and articulate against each other, lubricated by the synovial fluid inside the joint.

FIG. 3 also illustrates a slurry or matrix 34 which is loaded with transplanted chondrocyte cells; reinforcing runners 38 (patellar) and 58 (femoral), which connect the bases of the load-sharing runners, to provide them with additional reinforcement and support; a patellar positioning ring 40 and a plurality of patellar anchors 42; and, a femoral positioning ring 60 and a plurality of femoral anchors 62;

The semi-permeable membranes that will rest on top of the articulating surfaces of porous cell-growing scaffolds will provide certain highly useful protective and "dynamic loading" functions. These membranes will help shelter and protect cells that were seeded in the porous implant prior to the surgery, as well as cells that are reproduced and cartilage that is secreted in the implant after the surgery. In addition, these membranes will help distribute and balance the compressive loads that are imposed on the implant when the joint is being flexed and used, in a manner that is described below and illustrated in FIG. 5.

In addition, these semi-permeable membranes will allow the passage (in both directions) of water molecules and low-viscosity components of synovial fluid in a joint such as a knee, hip, or shoulder. These watery fluids (and dissolved compounds with low molecular weights) will be able to enter and pass through the porous scaffolding material, and the gel-like cartilage that will be generated by transplanted cells after surgery. This diffusion of only the watery (low-viscosity) fluids through the semi-permeable membrane will help provide the cells with nutrients and will help remove metabolic wastes, while causing the high-viscosity components of the synovial fluid to remain outside the membrane, where they will help lubricate the articulating surfaces in the joint.

Various methods can be used to assemble a scaffold-plus-membrane device. In one such method, illustrated in FIG. 4 scaffold subassembly 200 is made from an outer rim 210, two transverse runners 212 and 214, and a longitudinal runner 220. The runners 212 and 214, in conjunction with the rim 210, subdivide the area covered by scaffold subassembly 200 into six smaller areas, so that each smaller area can be filled with a cell slurry or a highly porous scaffolding material that will promote rapid cell growth and cartilage generation.

Figure 4:
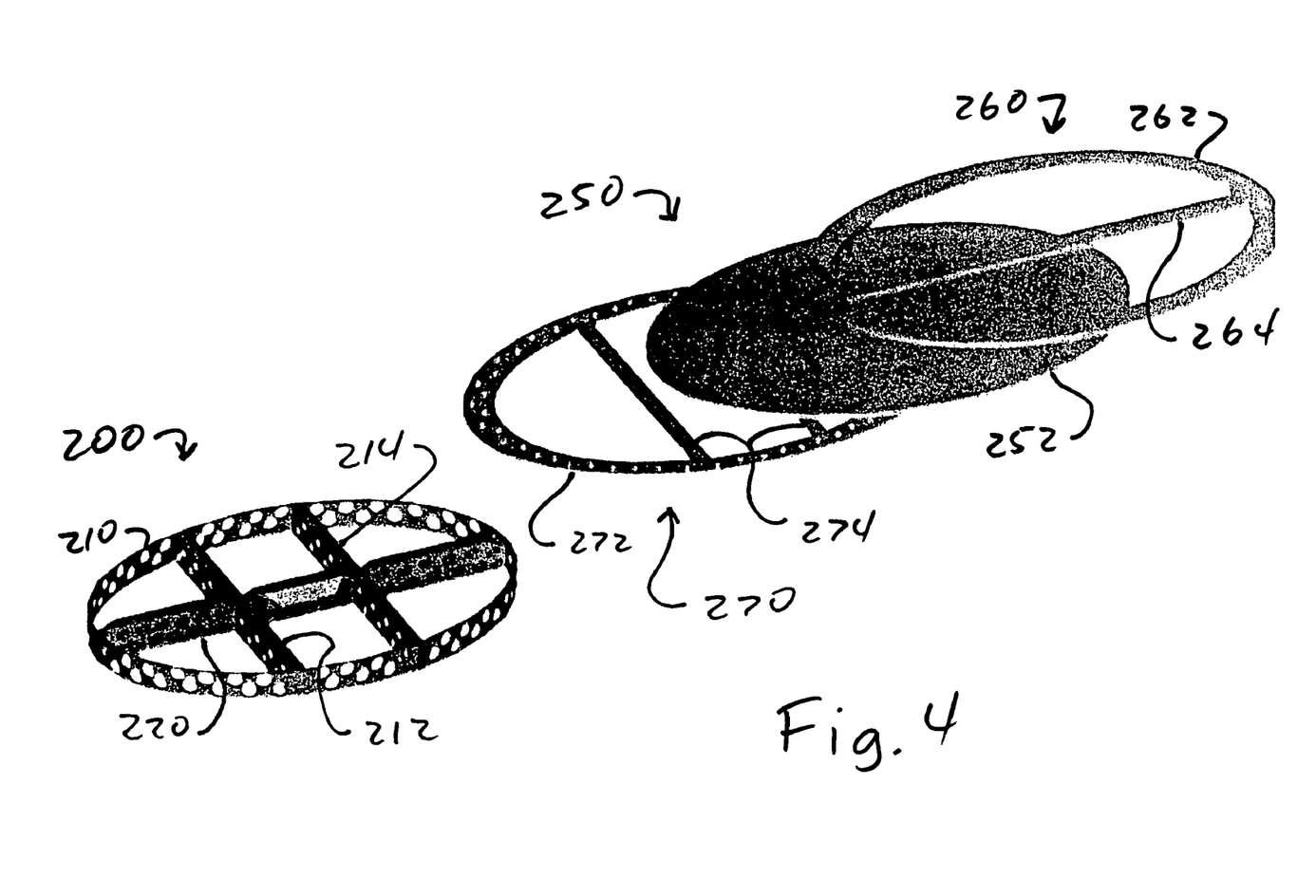
FIG. 4 depicts a selectively-permeable outer membrane which can be placed on the articulating surface of a resorbable scaffold of the type shown in FIGS. 1 and 2.

In a preferred embodiment, membrane assembly 250, also shown in FIG. 4, comprises three layers. The primary layer is a flat continuous membrane 252, which will cover the entire articulating surface of scaffold subassembly 200. In the configuration shown in FIG. 7 (which is one possible design out of numerous possible designs), membrane 252 will be "sandwiched" within, and supported and strengthened by, an upper layer 260 (with a rim 262 and at least one longitudinal runner 264) and a lower layer 270 (with a rim 272 and one or more transverse runners 274). All three layers which form lid assembly 250 are intended to be relatively thin, such as less than 1 or 2 mm around the rim, at the thickest aggregate part. The lid subassembly 250 is created outside the joint, and may be created by any of several possible methods (such as a sandwiching assembly operation, molding of a single integrated component, etc.).

The rims of the upper layer 260 and lower layer 270 (and possibly the runners 264 and 274 of the lower and upper layers as well), and one or more interacting components of the base assembly 200, will interact to provide a means for mechanically "snapping" the membrane subassembly 250 onto the scaffolding base subassembly 200. In some approaches, this type of "snapping" final assembly operation can be performed outside a joint that is being repaired; in other approaches, it might be performed inside the joint, after the base assembly has been completely positioned and anchored inside the joint and then filled, via an insertion cannula, with a paste, slurry, or other preparation of transplanted cells, or with a plurality of rapid-growth scaffolding segments that have been or can be seeded with cells.

It should also be noted that it is possible to use a snap-on lid assembly which places an "oversized" membrane over a scaffolding base assembly. In this type of approach, the center portion of the oversized membrane which covers and rests on top of the base assembly will be held in a relatively taut arrangement by the outer rim of the final assembly, while an additional portion of the membrane periphery can overlap beyond the outer rim of the base assembly. This design can be regarded as an "apron" membrane assembly. Such an apron can be designed to cover a cartilage area which has lost its normal surface membrane; because of the abrading process that leads to most cartilage defects, it is very common for a cartilage defect to be surrounded by a substantially larger area of damaged external membrane, which can be covered by an apron, as suggested above. If desired, such an apron can be tacked down, at one or more locations around its periphery, using previously developed devices, to further stabilize the grid lid and scaffold.

It should be noted that somewhat similar efforts have been made by earlier researchers, using entirely different technology, using pieces of harvested periosteum (a naturally occurring thin collagenous membrane which normally surrounds bones). Although those prior efforts have shown some limited success, fixation over large areas has proven very difficult. The techniques disclosed herein may permit the arthroscopic insertion of surface membranes over larger surface areas than have previously been feasible using either arthroscopic or open-surgical techniques. Accordingly, such approaches may deserve to be reevaluated in light of the technology disclosed herein.

It is anticipated that a surgeon who is ready to commence an implanting operation can have an assortment of scaffolds, with a variety of different sizes and shapes, each of which is contained in a sealed sterile package. Once the surgeon has entered the knee (or other joint) with arthroscopic tools, and has inspected the cartilage defect to see exactly how large it is, the surgeon can select a scaffold from the assortment that is available, and choose a scaffold having the best size and shape for treating that particular defect.

The surgeon will then prepare the area by removing a relatively small amount of existing cartilage which surrounds the defect, to prepare an exposed subchondral bone surface that can support the growth of new cartilage on its surface. This preparative step will typically use a scalpel and curette. If desired, the surgeon can also use other tools, such as a grinding burr to ensure complete removal of the cartilage from the prep area, a drill bit or piercing device to puncture the bone surface and ensure a blood supply to the implanted cartilage cells, etc.

Once the bone surface has been properly prepared by removing a small quantity of existing cartilage from around the defect, the flexible scaffold can be rolled or folded up, inserted into the knee or other joint (preferably through a minimally invasive incision), unfolded into its proper final shape, and positioned in the prepared area from which the damaged cartilage was removed, so that the bottom edges of the outer rim and internal runners of the scaffold press solidly against the prepared bone surface.

When the scaffold has been properly positioned inside the defect area, it can be anchored to the bone using any suitable type of pin, staple, or other anchoring device. A variety of such devices (including pins and staples made of resorbable material) are commercially available, and are used today for purposes such as anchoring a "flap" of cartilage to its bed so it can heal properly. Several anchoring sleeves 16 are shown positioned around the outer rim 14 of scaffold 10. If anchoring sleeves are used which extend to the full height of the scaffold, as shown, the upper (articulating) surface of each anchor sleeve preferably should be recessed, in a small circular area surrounding the hole, to accommodate a flattened circular anchor head that will fit snugly in the recessed space. Alternately or additionally, staples can be used to secure one or more "lesser" runners that do not rise up to the full height of the scaffold, as discussed below.

Placement of Membrane Directly on Native Cartilage

Figure 5:
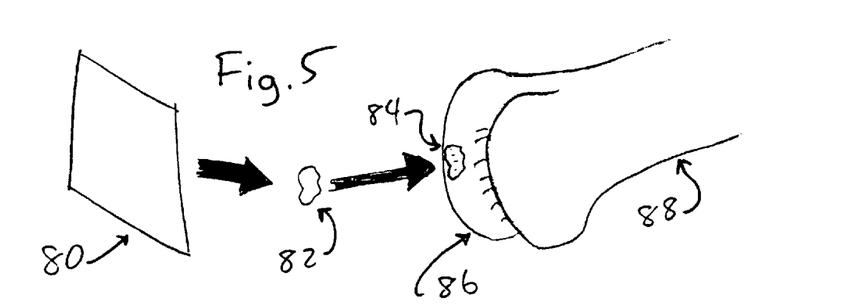
FIG. 5 depicts a membrane that has been secured on top of a mildly abraded natural cartilage surface, in a joint which suffers from chondromalacia.

In an alternate approach which does not involve an underlying scaffold implant, a semi-permeable membrane as disclosed herein can be placed directly on top of a slightly abraded or otherwise mildly damaged surface of a native cartilage segment which suffers from chondromalacia or a similar problem. This approach is illustrated in FIG. 5. In this highly simplified illustration, a large sheet of membrane material 80 is cut and trimmed by a surgeon to create a relatively small patch 82. Patch 82 is then secured to a damaged zone 84, on a femoral runner 86 of femur bone 88.

In most forms of chondromalacia, the damaged area takes the form of a zone which is slightly recessed, compared to the surrounding undamaged area. In some respects, it is analogous to a kitchen countertop, where a hardened smooth surface made of a waterproof material such as FORMICA™ has been chipped off, exposing a roughly circular or irregular patch of plywood or particle board which is part of the underlying structure. The exposed patch will be positioned in a shallow indentation. If a new piece of FORMICA™ can be cut and trimmed to the proper size, and then glued on top of the exposed patch of board, it will leave only a relatively small, thin seam between the surrounding undamaged FORMICA™ surface and the newly inserted patch material.

This same general type of approach is likely to be the best-suited method for applying most types of semi-permeable membrane patches, as disclosed herein, directly to a surface of a mildly damaged cartilage segment. As a general matter, in the absence of research results indicating the contrary, it is assumed to be unwise to try to use an artificial membrane to cover up an intact, properly functioning, and healthy portion of a cartilage surface. Only the damaged area will be treated, and that area either (i) will be already positioned in a suitable indentation, when the surgeon reaches it, or (ii) can be cut, trimmed, and/or cleaned out by the surgeon, in any way necessary to establish a recessed area with a desired size, shape, and depth.

Once the defect area has been properly accessed, prepared if necessary, and measured, a membrane segment can be trimmed to the proper size and shape, by the surgeon, outside the joint. After a patch of membrane material having the desired size is ready, it is then inserted into the joint, positioned over the defect, and checked for size and shape. When the surgeon decides it is ready, it is then secured to the defect area, using any of several methods, preferably in combination with each other. Suitable attachment methods include resorbable sutures (which can penetrate the surrounding healthy cartilage, fibrin cement, and possibly anchoring pins (made of resorbable material if desired) that can be driven into the underlying bone.

Another method of adhesion which may be highly useful in this approach involves molecular-scale penetrating agents. Unlike cements, most of which form tight covalent bonds but only with surface molecules, penetrating agents can use molecules that are comparable to extremely small VELCRO™-type hooks. These can penetrate a short distance into the gel-like substance of underlying cartilage, and bind to the collagen and other molecular strands and fibers that form the porous network which holds together the hydrogel structure of cartilage. Such binding reactions might use any of several types of molecular attraction, adhesion, or clinging that are known to polymeric scientists, including (i) entangling of non-linear molecular chains, especially complementary chains that tend to attract each other; (ii) ionic, hydrogen-bonding, or similar attractions between negatively and positively charged atoms or groups in different molecular chains; and (iii) use of molecular-scale "barbs" (including molecules modelled after natural systems, such as the hemagglutinin protein of influenza viruses), which can be pressed into effectively pointed structures when compressive force is applied, but which will open up into larger entangling pendant groups when tension is applied.

Regardless of how the membrane is used, it must be suited in all respects for implantation into a mammalian joint in a surgical procedure. The full scope of the requirements that contribute to this status are well-known to companies that manufacture surgical implants, and only one is worth mentioning in specific. Any such membrane normally must be maintained, during storage and shipping, in a sealed package which ensures sterility of the membrane until use in a surgical procedure.

Load-Distributing Properties of Semi-Permeable Membranes

If a semi-permeable membrane is secured to the articulating surface of either (i) a cell implantation scaffold, or (ii) a surface-damaged native cartilage segment, the membrane can provide implanted chondrocyte cells with additional protection from the various loads and stresses that are imposed on underlying scaffold or cartilage.

In addition, if an articulating membrane is designed and manufactured properly, with suitable degrees of fluid permeability and flexibility, it can help ensure that weight-bearing loads are distributed and imposed evenly on all of the runner compartments, to help ensure that cartilage which is regenerated in the scaffold compartments has a more uniform and consistent density and firmness.

To better understand the types of membranes preferred for use as disclosed herein, a working knowledge of certain physiological and fluid-flow aspects of healthy and unmodified cartilage surfaces in a joint such as a knee is necessary. The overview provided below (which is necessarily brief and highly simplified), and the illustrations in FIGS. 6A through 6E, are an analysis by the inventor/applicant herein, based upon numerous published articles, and on his own insights as a physician and surgeon who has worked in this areas for years.

The published articles in this field can be grouped into three major categories. In the first category, articles which focus mainly upon non-fluid structural components of cartilage (either in naturally-occurring healthy form, or in diseased form) include Teshima et al, *J Bone Joint Surg Br* 77: 460 (1995), and Guilak et al, J Orthoped Res 12: 474 (1994).

In the second category, articles that focus mainly on the liquids which help lubricate a joint, or on the interactions between liquids and various fibers, membranes, etc., include Setton et al, *J Biomech* 26: 581 (1993), Oloyede et al, *Connect Tissue Res* 29: 251 (1993), Bernich et al, *Biochim Biophys Acta* 448: 551 (1976), Torzilla, *Med Biol Eng Comp* 31 *Suppl*: S93 (1993), Oloyede et al, *Connect Tissue Res* 30: 127 (1993), Murakami et al, *Proc Inst Mech Engr [H]* 212: 23 (1998), Hou et al, *J Biomech* 25: 247 (1992), Hlavacek, *J Biomech* 28: 1199 (1995), Higaki et al, *Proc Inst Mech Engr [H]* 212: 337 (1998), Williams et al, *Proc Inst Mech Engr [H]* 207: 59 (1993), Schwarz et al, *Br J Rheumatol* 37: 21 (1998).

In the third category, articles which focus on artificial devices that have been developed in the past (including artificial joints, candidate materials for use in joint repair, and cellular transplants) include Fisher et al, *Proc Inst Mech Engr [H]* 205: 73 (1993), Unsworth, *Proc Inst Mech Engr [H]* 205: 73 (1991), Williams et al, *Biomaterials* 16: 1169 (1995), Auger et al, *Proc Inst Mech Engr [H]* 207: 25 (1993), McClure et al, *Proc Inst Mech Engr [H]* 210: 89 (1996), Stewart et al, *Proc Inst Mech Engr [H]* 211: 451 (1997), Williams et al, *Proc Inst Mech Engr [H]* 211: 359 (1997), Gu et al, *Biomed Mater Engr* 8: 75 (1998), Ambrosio et al, *Proc Inst Mech Engr [H]* 212: 93 (1998), Corkhill et al, *J Biomater Sci Polym Ed* 4: 615 (1993), Oxley et al, *Biomaterials* 14: 1064 (1993), Badiger et al, *Biomaterials* 14: 1059 (1993), Szleifer, *Biophys J* 72: 595 (1997), Baker et al, *Cell Transplant* 6: 585 (1997), and Dror et al, *Biomater Devices Artif Organs* 7: 31 (1979).

The full titles and abstracts of all of these articles (and, indeed the complete texts of many of the articles they are abstracted from) can be obtained for free through the Internet, using one of the National Library of Medicine's search engines, such as at http://www.ncbi.nih.gov or http://www.igm.nih.gov.

Several acronyms and abbreviations that are commonly used in these and similar articles are worth noting, as follows: SF, synovial fluid; HA, hyaluronic acid, and its ionized or salt form, hyaluronate; DPPC, dipalmitoyl phosphatidyl-choline; SAPL, surface-active phospholipid; IPN, inter-penetrating network.

Briefly, the major components of synovial fluid (SF) inside a joint (such as a knee joint, which is used for purposes of illustration) include the following:

(1) water, which should be regarded as both a lubricant and as a solvent fluid, and which contains and carries various "macromolecules" that make the lubricant more slippery and viscous than plain water.

(2) hyaluronate (HA) molecules. These are naturally occurring polymers, with molecular weights ranging from about 50,000 up to about 8 million daltons. A molecule of hyaluronate normally is formed by stringing together a large number of alternating rings of glucosamine and glucuronate.

(3) monomeric and short-chain forms of glucosamine, glucuronate, chondroitin, and other relatively small molecules that form the building blocks of cartilage, hyaluronate, and other naturally-occurring compounds; and, (4) two compounds called "lubricin" and "surface-active phospholipid" (SAPL). These two types of molecules exist in both free form, and in a "complex" form that is held together by inter-molecular attraction rather than covalent bonding. In a lubricin/SAPL complex, a single molecule of lubricin is assumed to bind to a single molecule of SAPL. A lubricin/SAPL complex can be sheared apart or otherwise pulled apart by fluid flow or mechanical stress, without damaging either type of molecule. After this type of separation, it is assumed that the free molecules of lubricin and SAPL can recombine again, in solution.

Those are the primary known lubricating components of synovial fluid which are essential to understanding the statements and proposals in this application. They're shown in simplified schematic form in FIGS. 6A through 6E.

Figure 6A:
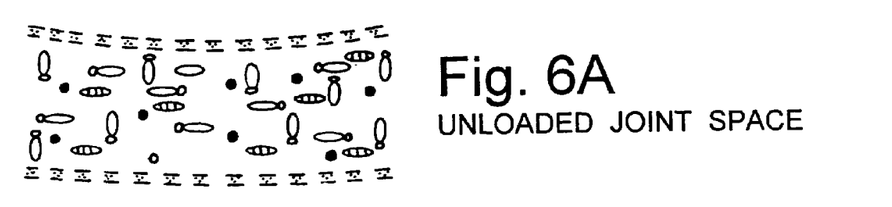
FIG. 6 (which includes parts 6A through 6E) depicts several natural physiological processes that are emulated by a selectively-permeable membrane, which can be mounted on top of an implantable cell-growing scaffold, as shown in FIG. 2, or secured on top of a mildly abraded cartilage surface as a protective layer.

FIG. 6A, labelled "Unloaded Joint Space", is a cross-sectional depiction of a small portion of a knee joint that is relaxed and not under pressure. The top and bottom "semi-permeable" membranes shown in FIGS. 6A through 6E represent only the outermost membranes that cover the opposing surfaces of two different segments of cartilage, on two different bones. In each part of FIG. 6, the upper membrane covers the bottom surface of a femoral runner, while the lower membrane covers the upper surface of a tibial plateau.

As indicated in FIGS. 6A-E, these two membranes do not contact each other at all; instead, there is a gap between them. That gap is filled with synovial fluid, which contains water (the solvent) and the slippery components of a biological "soup", which includes hyaluronate molecules, lubricin/SAPL complexes, and various other molecules such as glucosamine, chondroitin, etc.

The outermost membranes which cover the femoral and tibial cartilage segments are "selectively permeable". In general, each cartilage membrane is composed of a thin layer, made up mainly of interconnected collagen fibers. Collagen is a fibrous protein, which forms the matrix that holds cells together in nearly all types of cohesive flexible tissue, including muscle tissue, skin, organs, etc. Each thin membrane made of interconnected collagen fibers allows water molecules to flow through it in a rate-controlled manner; as discussed below, this allows fluid loads and pressures to be redistributed across the membrane in a regulated manner as the joint is "loaded" with weight.

Each collagen membrane also allows some but not all of the "macromolecules" which lubricate the joint to permeate through that membrane. The massive hyaluronate molecules are assumed to not penetrate or permeate through the membranes at all, while the smaller building blocks of cartilage (such as glucosamine and chondroitin) can gradually permeate through the membranes, allowing them to reach the cartilage beneath the membranes. The exact relationship between the membrane and the different components of the lubricin/SAPL complexes is not yet fully understood; however, for purposes of the following simplified description, it is assumed that the lubricin molecules can either penetrate the collagenous membrane, or at least partially enter that membrane, while the SAPL molecules do not penetrate or enter the membrane at all (at least, not in substantial quantities).

Figure 6B:
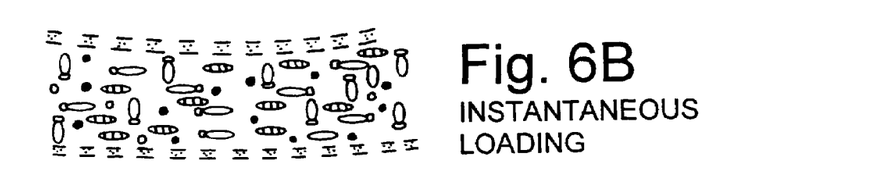

FIG. 6B (labelled "Instantaneous Loading") illustrates what happens when the joint is initially compressed after being at rest, such as when the person stands up. As the person goes through the motion of standing, the bottom surface of the femoral runner begins to slide toward the rear, on the tibial plateau. As this type of sliding motion occurs, pressure is imposed on the joint, due to the weight of the person.

During this initial sliding and loading motion, within the zone of highest pressure within the joint, the cartilage surfaces on the femur and tibia initially engage in a "hydroplaning" motion. As this is occurring, the macromolecules in the synovial fluid are being compressed, as shown by their slightly greater density in FIG. 6B compared to the fluid in the relaxed joint of FIG. 6A. However, these macromolecules have not yet had time to begin permeating into either of the cartilage membranes, and the much smaller water molecules have had only an instant to commence that process. The two cartilage membranes do not contact each other during this "hydroplaning" stage; instead, the femoral runner is kept suspended above the tibial plateau by the layer of watery synovial fluid between them.

Figure 6C:
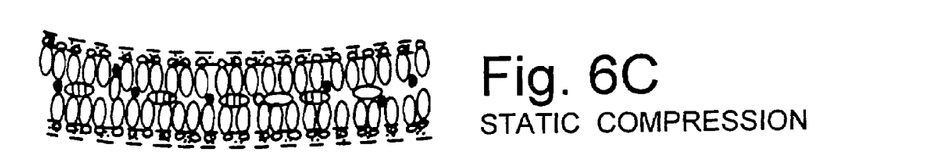

FIG. 6C ("Static Compression") schematically illustrates the condition that will arise within the zone of maximum compression inside the joint, if the person remains standing still for several minutes. Under sustained static pressure, the lubricin/SAPL complexes, which are forced to seek an arrangement that minimizes their volume, begin to line up in an aligned configuration as shown. The lubricin "heads" will, to at least some extent, contribute to this alignment between the cartilage membranes; although this process is not fully understood, it is assumed herein, for purposes of discussion and illustration, that the lubricin heads will fit into the interstitial spaces between adjacent collagen fibers in the cartilage membranes, and the SAPL "tails" project will away from the membrane, into the synovial fluid. In addition, this type of static compression will also tend to drive water molecules (which are much smaller and more mobile) out of the high-pressure zone with maximal compression, thereby increase the concentration of the remaining lubricant components in that zone, which will increase the thickness and viscosity of the lubricant fluid that remains.

Figure 6D:
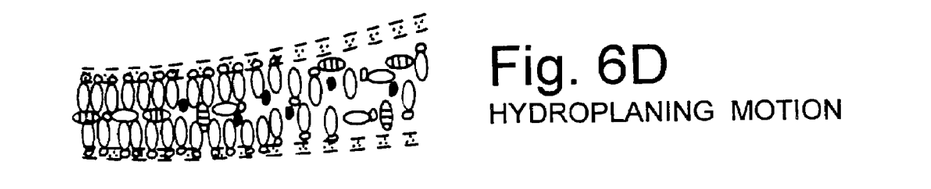

FIG. 6D ("Hydroplaning Motion") illustrates what happens if the person then begins walking forward, after standing still for a sustained period. Shear forces exerted on the synovial fluid by the relative motion of the two membranes cause the SAPL/lubricin concentrate in the contact zone to lubricate the initial launch of the joint into a hydroplaning mode of load transfer. As mentioned above, this type of action may cause at least some of the lubricin/SAPL complexes to be pulled apart or otherwise altered.

These various actions (including possible dissociation of SAPL from lubricin, mixing of the SAPL molecules with hyaluronate, and removal of water and other small solute molecules from the high-pressure zone) lead to formation of a highly viscous, slippery, "slimy" fluid between the two cartilage segments, when the person is standing still. Upon initiation of walking, the surfaces begin a "hydroplaning" interaction relative to each other, and thereby promote the clearing of the surface membranes for future alignment of lubricin/SAPL complexes when the joint is subsequently statically loaded.

Because of its viscous and slimy nature (and, it is hypothesized herein, because free SAPL molecules in the viscous fluid may be attracted to lubricin molecules that have become embedded in the surfaces of the cartilage membranes), the lubricating components of the synovial fluid (mainly hyaluronate and SAPL molecules) continue to keep the two cartilage segments separated from each other, so that the two opposing cartilage segments still do not directly contact each other, even if the person continues to walk or run. This is part of a natural mechanism of fluid cushioning and fluid insulation, which allows cartilage segments in knee and hip joints to remain intact, undamaged, and unabraded, despite all the wear and motion that is imposed on those joints for 70 or 80 years or more, in a healthy person.

Figure 6E:
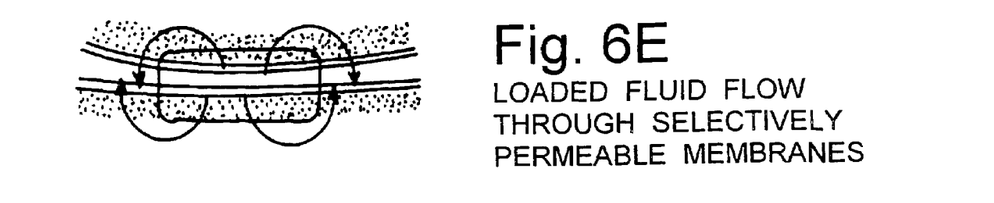

FIG. 6E depicts another apparently important factor in a "tribological" analysis of how synovial fluids can manage to lubricate knee and hip joints so successfully (for the most part) for decades. There are 4 semi-circular arrows shown in FIG. 6E. These arrows schematically depict pressures and directional fluid flows, across the two membranes that cover the cartilage segments. These arrows indicate that, in the regions which surround and flank the center of a high-pressure loading zone, water molecules inside the cartilage "gel" (beneath the covering membranes) in each segment of cartilage are being forced out and away from the central zone where the pressure is highest. These water molecules can flow through the gel, but only slowly, because the fibrous molecular matrix that holds the gel together constrains molecular flow through the gel.

As water molecules in the area of highest pressure inside a knee joint do their best to shift and flow outwardly into the flanking areas, they exert pressure against the surrounding water molecules, which fill the cartilage gel that surrounds the highest pressure region. As indicated by the arrows in FIG. 6E, this type of pressure, acting on small and mobile water molecules that are trapped inside a segment of cartilage gel, causes the semi-permeable membranes which cover the two cartilage segments to be pushed toward each other, from beneath, rather than away from each other, in the areas that flank and surround the center zone of highest pressure.

This type of fluid response, by small and semi-mobile water molecules trapped inside a gel structure, causes two important results. The first involves a more even distribution of pressure within a weight-bearing joint, such as a knee joint in a person standing upright. Since the pressures and constrained motions of water inside a cartilage gel cause the surrounding areas of cartilage to press outwardly, away from their bones, those surrounding regions will help support and bear a larger portion of the weight that is being imposed on that knee joint. This type of cooperative assistance, by a roughly ring-shaped circle of cartilage surrounding the center zone of maximum pressure, helps ensure that no single small area of cartilage is forced to bear the entire weight of a person's body. Obviously, this type of pressure-sharing response is important in helping prevent potentially abrasive and destructive direct contact between two opposing segments of cartilage in a knee or hip joint.

The second effect may be equally important, on a long-term basis. The flow of small and mobile water molecules, within the cartilage gel, helps free embedded macromolecules (including lubricin molecules) from the semi-permeable collagenous membrane which covers a cartilage segment. In other words, the motion of water molecules within and through cartilage gel may help "blow out" and rinse out the selectively permeable collagen membrane that covers that segment of cartilage; this can dislodge and remove any lubricin, SAPL, hyaluronate, or other macromolecules that have become embedded in the semi-permeable collagen membrane, and may help clear the membrane for subsequent interactions with fresh lubricin/SAPL complexes. This type of constrained flow of small water molecules through a gel matrix may also help generate and ensure substantially higher levels of travel and permeation of the nutrient building blocks (including glucosamine and chondroitin) through both the semi-permeable membrane which covers a segment of cartilage gel, and through the cartilage gel itself.

All of these factors contribute to an understanding of the type of selective permeability that is required of a membrane designed for use in repairing cartilage as disclosed herein.

Resorbing, Non-Resorbing, and Transforming Membranes

At least three different types of semi-permeable membranes can be manufactured for use as disclosed herein. The preferred type that will give the best results in a specific repair operation on a specific patient can be determined by the surgeon treating that patient. The three categories of articulating membranes are referred to herein as resorbing membranes, non-resorbing (or permanent) membranes, and transforming membranes.

A resorbing membrane is designed and intended to be gradually digested and dissolved, mainly by extracellular enzymes, so that it will disappear and be replaced by a natural biological surface. Because the remnants of a partially-digested membrane may act as debris that may clutter up or even damage the articulating interface during the intermediate stages of degradation, this approach generally is not regarded as the most initially promising approach for this type of joint repair, especially in knee joints. However, resorbing membranes may be useful in other joints, and they can be tested and evaluated in any type of joint, including knee joints, using lab animals. If good results are obtained in animal tests, this approach may be quite valuable, especially if a resorbable membrane can be developed which, without generating particulate debris, will instead act as though it has become permanently cemented to the surface it contacts, so that any digestion byproducts will diffuse in a direction that carries it into the cellular matrix and toward the bone surface that supports that membrane, without releasing debris into the synovial fluid that lubricates an articulating surface between two cartilage layers.

A permanent membrane is designed and intended to remain in the joint for the entire remaining life of the patient, in an essentially unmodified form. As such, it must be completely non-resorbable and highly resistant to biological degradation. Various types of already known non-resorbing biocompatible synthetic polymers can be used for such purposes.

In one preferred embodiment, if a membrane of this nature is to be placed on top of a cell-growing scaffold, a permanent synthetic membrane can be cemented to the upper surfaces of the resorbable rim and runners, so that the supporting rim and runners will be gradually resorbed and replaced by newly-generated cartilage, while the permanent membrane remains intact as the articulating surface layer which covers and protects the supporting structures. In an alternate preferred embodiment, a permanent synthetic membrane can be permanently supported by a set of non-resorbable runners, presumably made of the same type of non-rigid synthetic polymer, so that the articulating membrane and runners all remain in essentially unchanged condition inside the joint, while the transplanted chondrocyte cells generate additional cartilage that will provide additional support and stability for the permanent membrane.

In either of these situations, the synthetic polymer will need to be porous and permeable to water molecules and to low-molecular-weight solutes dissolved in water. One type of synthetic polymer with these traits, which offers good promise and should be evaluated as a candidate for use in this type of membrane, is a copolymeric blend of poly-vinyl alcohol (abbreviated as PVA) and poly-vinyl pyrrolidone (abbreviated as PVP). As discussed in articles such as Peppas 1987, Nishio et al 1990, Zhang et al 1992, Hickey et al 1995, and Cassu et al 1997 and 1999, membranes made of PVA/PVP blends can be made with a desired range of pore sizes, without using potentially toxic initiators, cross-linkers, or other chemical agents that might leach out of the final product if used during manufacture.

Numerous other biocompatible hydrophilic polymers have been developed for surgically implanted devices, and manufacturing techniques are known for making porous films or other articles from such polymers. In addition, intensive research is constantly being done at universities, medical schools, and private companies, on improved molecular combinations, improved manufacturing techniques, and improved methods of modifying and adapting already-known polymers to new and emerging uses. Accordingly, any such polymer compound which is currently known or hereafter discovered, and which has a proper combination of hydrophilicity, permeability, biocompatibility, non-rigid hardness, and durability, can be evaluated for use as a semi-permeable surface layer on a cartilage replacement implant as disclosed herein, using no more than routine experimentation.

A transforming membrane is also designed to remain inside the joint for the life of the patient; however, unlike a synthetic permanent membrane, it will be acted upon by cells and enzymes in ways that convert it into a modified final form. This type of membrane can take advantage of certain healing and regenerating activities that occur after a bone has been broken, when the damaged tissue must repair itself and regenerate a fully healed and functional bone surface with a "periosteal" membrane covering the surface of the bone.

To create a transforming membrane, a segment of periosteal or perichondrial membrane can be harvested from elsewhere in the patient's body (or from another source, as discussed below). Under laboratory conditions, this membrane segment (which will already contain some chondrocytes and stem cells) can be saturated, coated, or otherwise loaded with a liquid that contains both (i) mesenchymal "stem cells" that will transform into chondrocytes if contacted by certain hormones that act as "transforming factors"; and (ii) various naturally-occurring compounds such as collagen, "procollagen" building blocks, glycosaminoglycans, and other components that are converted and assembled by cells into load-bearing structural components such as cartilage. Under the proper conditions, after implantation into a load-bearing joint, the chondrocytes or stem cells that are on or in the implanted membrane segment will begin to organize the available biomaterials into a load-bearing surface, effectively using the implanted segment of membrane in a manner analogous to a canvas that an artist uses to create a painting.

Under the current state of the art, which is limited to repairing only relatively small defects, most chondrocyte transplant procedures require elaborate steps to harvest a small piece of periosteal tissue from somewhere in the patient's body, so it can be used for the procedure. However, methods have been developed in other fields of surgery (most notably involving replacements for damaged heart valves) for chemically treating tissues segments that have been harvested from human cadavers, or even from completely different species (mainly pigs). This type of chemical treatment for "allograft" or "xenograft" tissue can likely be adapted to develop effective ways of treating large segments of periosteal or perichondrial membrane harvested from cadavers or animals, in ways that will render such treated membranes suitable for transplantation into a knee or other joint, to create a "transforming membrane" as described herein. U.S. Pat. Nos. 4,627,853 (Campbell et al 1986) and 5,782,915 (Stone 1998) describe various methods that can be used to treat bone or cartilage tissue from cadavers or non-human species, to render the treated tissue non-immunogenic and suitable for transplanting into humans. It should also be noted that substantial efforts have been made to genetically engineer certain types of animals, so that tissues harvested from the animals will have reduced antigenicity and will be less likely to provoke an immune response if implanted into a human. Such efforts are discussed in articles such as Rosengard et al 1992.

The proper selection of a resorbing, non-resorbing, or transforming membrane for repairing a specific joint in a patient will depend on factors that will need to be evaluated on an individual basis, for each patient, by the surgeon treating that patient. The factors that will be relevant in reaching such decisions include: (i) which joint is involved, and what types of stresses it is subjected to in that particular patient; (ii) the etiologic factor which caused the cartilage damage; (iii) the condition of the joint, and of the damaged cartilage segment (s) in that joint; and, (iv) the size, weight, age, lifestyle, physical activity level, and overall medical condition of the patient.

Membrane Created by Surface Treatment of a Hydrogel

Another method that can be used to create a semi-permeable surface membrane as disclosed herein involves a surface treatment of a permeable material that has substantial thickness, such as a hydrogel, to create an altered membrane-type structure on the surface of the permeable material.

This type of surface treatment can use any of various methods known to chemists, including: (i) chemicals, comparable to the chemicals used in "tanning" leather or other biological materials to make them tougher and more durable; (ii) heating or freezing, in a manner comparable to a cycling form of freezing and thawing that is used to create desired traits in copolymeric blends of poly-vinyl alcohol and poly-vinyl pyrrolidone; (iii) ultraviolet, microwave, or other radiation, which can be controlled in a way that will effectively "cook" a surface layer without penetrating deeply into the treated material; or, (iv) a combination of such methods, such as using high temperature or radiation to treat a hydrogel that has been coated with, soaked in, or otherwise surface-treated by a crosslinking compound or other chemical which will undergo a reaction when catalyzed by the temperature, radiation, or other physical manipulation.

In addition, a similar approach may be used to create a membrane only, in a two-stage process in which: (i) a relatively thick hydrogel or other soft material is surface-treated, in a manner which creates a relatively tough surface membrane; and, (ii) the still-soft material that remains below or inside the toughened surface membrane is then removed, by means such as pressurized washing, mild abrasion or scraping, etc., leaving behind the toughened membrane.

Materials for Manufacturing Membranes

If a membrane is used to help repair an articulating cartilage surface, it must have a combination of traits that will allow it to function adequately as a new articulating surface in that joint. The primary desirable traits include: (i) a very smooth surface, to promote sliding and articulation with very little friction, resistance, "grabbing," or abrasion; (ii) a hydrophilic nature, to ensure constant wetness and lubrication of the articulating surfaces by the naturally occurring synovial fluid in a joint; (iii) physiological acceptability and biocompatability, which requires that it must not provoke blood clots, an immune rejection response, or other adverse events known to those who specialize in biocompatible implants; and (iv) permeability to synovial fluid nutrients.

A membrane with these traits can be composed of suitable fibers, made of collagen or a suitable resorbable, hydrophilic, synthetic polymer. Preferably, the membrane should be woven or otherwise fabricated such that the fibers are oriented parallel to the articular surface (i.e., in the "tangential" orientation).

If any slight roughness results from the weaving process or other fabrication method, the direction and side having the highest level of "smoothness" should be oriented along the primary direction of travel (for example, the anterior-posterior direction, in a femoral runner or tibial plateau). In conventional fabrics, the level of smoothness in the four major "planes" of a piece of cloth can usually be felt by rubbing a hand across the surface of a cloth, in both of two perpendicular directions, each on both sides of the piece of cloth. In much finer fabrics, the maximally smooth surface and direction can be determined by rubbing a coarse piece of cloth or wire mesh against the fabric in each major direction, and measuring the resistance in each direction.

If desired, the undersurface of the membrane can be provided with interwoven fibers that extend downward, generally perpendicular to the membrane surface (referred to as the "radial" direction, since most cartilage surfaces are generally round). These radially extending fibers will facilitate the interdigitation of these fibers into the residual cartilage radial layer. As mentioned above, such radial fibers on the undersurface of a membrane can be provided with hooked or barbed type structures, to promote a "velcroid" type of adherence of the membrane to the collagen (and, to a lesser extent, glycosaminoglycan) fibers which hold together the cartilage hydrogel, at the depths of the residual chondral radial layer.

Alternately or additionally, various adhesive compounds (such as fibrin and/or collagen glue) and mechanical devices (such as anchor pins, staples, sutures, etc.) can also be used to help secure a membrane to a cartilage surface or scaffold implant.

If desired, mesenchymal stem cells (which can be obtained most easily from bone marrow aspirates) can also be used to populate a membrane undersurface, prior to or during surgical implantation.

As noted above, any selectively-permeable membrane for use as disclosed herein should be permeable to water, normal nutrients with low molecular weights, and low-molecular-weight cellular waste products. However, such a membrane should be impermeable to surface-active phospholipids, hyaluronic acid, and the other macromolecular components of synovial fluid (which, in a healthy joint, stay outside of the cartilage hydrogel, and remain dissolved or suspended in the synovial fluid between two cartilage surfaces).

Semi-Permeable Membranes for Internal Organ Repair

The study and realization, by the Inventor/Applicant herein, of the crucial roles that a selectively permeable bidirectional membrane plays in healthy cartilage has also led to an enhanced appreciation of the role that a surrounding selectively permeable bidirectional membrane is likely to play in other types of surgery which use resorbable scaffolds. Such scaffolds, which can be seeded with any selected type of cells, are actively being studied and developed for use in regenerating or repairing internal organs (such as a liver, spleen, pancreas, etc.) or other organized tissues (efforts are even being made to generate replacement hearts or heart tissue).

Accordingly, the technology discussed herein can also be adapted for use in tissue regeneration efforts using resorbable scaffolds to repair, regenerate, replace, or supplement internal organs. Such a surface membrane can be provided on one or more surface areas of the resorbable scaffold, and in the case of an internal organ, can provide a capsule which encloses essentially the entire resorbable scaffold. Once in place, the membrane can facilitate the absorption and retention of nutrients and functional molecules in one direction, and the release of waste and various functional molecules (such as hormones, metabolites, etc.) in the other direction, by the regenerating tissue, while at the same time using its selective permeability to help sustain the desired homeostatic balances and concentrations of various types of macromolecules in fluids on both sides of the membrane.

In addition, any such membrane can be seeded with one or more selected types of stem cells, either prior to the surgery or during the surgical implantation procedure, on the interior side of the membrane (i.e., the surface which contacts the resorbable scaffold). Such stem cells, if properly selected for a particular use, can help accelerate and promote rapid and effective healing, and can help minimize the formation of scar tissue.

Accordingly, this disclosure includes a membrane segment for use in surgically treating an internal organ in conjunction with a resorbable cell-growing matrix, comprising a membrane segment which is porous and hydrophilic and which is permeable to water and to low molecular weight nutrients dissolved in water, wherein the membrane segment (a) is maintained during storage and shipping in a sealed package which ensures sterility of the membrane until use in a surgical procedure; (b) is suited in all respects for implantation into a mammalian body in a surgical procedure; (c) has little or no permeability to biological compounds having a molecular weight greater than about 5000 daltons; and, (d) has an anchoring surface suited for direct contact with a resorbable cell-growing matrix that can be seeded with viable cells, and a second opposed surface which will remain internally exposed, on a surface of an internal organ, after the resorbable cell-growing matrix has been implanted in a body. This disclosure also includes a resorbable cell-growing matrix for use in surgically treating an internal organ, wherein at least one surface of the resorbable cell-growing matrix is covered by a membrane segment which is porous and hydrophilic and which is permeable to water and to low molecular weight nutrients dissolved in water.

Thus, there has been shown and described a new and useful type of semi-permeable membrane for use in surgery, especially in surgical repair of damaged or diseased cartilage. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Cassu, S. N., et al, "PVA and PVP blends: 1. Miscibility, microheterogeneity and free volume change," *Polymer* 38: 3907-3911 (1997)

Cassu, S. N., et al, "PVA and PVP blends: 2. Study of relaxations . . ." *Polymer* 40: 4845-4851 (1999)

Hickey, A. S., et al, "Mesh Size and Diffusive Characteristics of Semicrystalline PVA Membranes Prepared by Freezing/Thawing Techniques," *J. Membr. Sci.* 107: 229-237 (1995)

Nishio, Y., et al, "Miscibility and Orientation Behavior of PVA/PVP Blends," *J. Polym. Sci., Polym. Phys. Ed.* 28: 355-376 (1990)

Peppas, N. A., "Hydrogels of PVA and its Copolymers," in Peppas, ed., *Hydrogels in Medicine and Pharmacy*, Vol. 2, 1-48 (CRC Press, Boca Raton, Fla., 1987)

Rosengard, B. R., et al, "Selective breeding of miniature swine leads to an increased rate of acceptance of MHC-identical, but not of class I-disparate, renal allografts," *J. Immunol.* 149: 1099-103 (1992)

Zhang, X., et al, "High-resolution solid state 13C nuclear magnetic resonance study of PVA/PVP blends," *Polymer* 33: 712-716 (1992)

The invention claimed is:

1. A semi-permeable membrane segment that is attached to a surgical implant that comprises a hydrogel material, wherein said surgical implant comprising said hydrogel material and said attached membrane segment is sized and configured for replacing damaged cartilage in a mammalian joint, and wherein said semi-permeable membrane segment is attached to said hydrogel material in a manner which provides an articulating surface of the surgical implant, wherein said articulating surface of said surgical implant is designed to interact with water, surface-active phospholipid molecules, and hyaluronate molecules in mammalian synovial fluid, after surgical implantation of said surgical implant into a joint, in a manner that sustains lubrication of said articulating surface by said water, surface-active phospholipid molecules, and hyaluronate molecules, and wherein said semi-permeable membrane segment is hydrophilic and permeable to water but not permeable to surface-active phospholipid or hyaluronate molecules in mammalian synovial fluid.

2. The hydrogel material of claim 1, wherein said articulating surface is created by chemical treatment of at least one surface of said hydrogel material.

* * * * *